United States Patent [19]

Brazdil, Jr. et al.

[11] Patent Number: 4,871,706

[45] Date of Patent: Oct. 3, 1989

[54] CATALYST FOR THE AMMOXIDATION OF PARAFFINS

[75] Inventors: James F. Brazdil, Jr., Mayfield Village; Linda C. Glaeser, Lyndhurst; Mark A. Toft, Lakewood, all of Ohio

[73] Assignee: The Standard Oil Company, Cleveland, Ohio

[21] Appl. No.: 133,661

[22] Filed: Dec. 16, 1987

[51] Int. Cl.$^4$ .................. B01J 23/18; B01J 27/16; B01J 27/188; B01J 27/198

[52] U.S. Cl. ............................. 502/209; 502/202; 502/204; 502/206; 502/207; 558/319; 558/322; 558/323; 558/325

[58] Field of Search ............ 502/202, 204, 206, 207, 502/209, 215, 306, 307, 310, 312; 558/319, 322, 323, 325

[56] References Cited

U.S. PATENT DOCUMENTS

| | | | |
|---|---|---|---|
| 3,860,534 | 1/1975 | Harris et al. | 502/353 |
| 3,988,359 | 10/1976 | Saito et al. | 502/204 X |
| 4,436,671 | 3/1984 | Furuoya et al. | 558/319 |

FOREIGN PATENT DOCUMENTS 1336136 11/1973 United Kingdom ............... 558/319

Primary Examiner—W. J. Shine
Attorney, Agent, or Firm—C. S. Lynch; D. J. Untener; L. W. Evans

[57] ABSTRACT

Disclosed is the reaction of $C_3$ to $C_4$ paraffins with $O_2$ and $NH_3$ to make $\alpha,\beta$-unsaturated nitriles and olefins, using certain complex metal oxide catalysts containing V, Sb, W and certain optional elements.

4 Claims, No Drawings

CATALYST FOR THE AMMOXIDATION OF PARAFFINS

This invention relates to the catalytic ammoxidation of paraffins containing from 3 to 4 carbon atoms to α,β-unsaturated mononitriles. Most important is the ammoxidation of propane to acrylonitrile and isobutane to methacrylonitrile, especially the former.

Because of the price differential between propylene and propane an economic incentive exists for the development of a viable catalytic process for conversion of propane to acrylonitrile.

In application Ser. No. 724,226, filed Apr. 17, 1985, now U.S. Pat. No. 4,746,641, are disclosed and claimed catalysts containing Sb and V in atomic ratios of Sb:V>1, together with at least one other cation and oxygen, supported on an inorganic oxide support that improves catalytic activity. These catalysts are used for the reaction of paraffins with ammonia and oxygen to make nitriles plus olefins; especially to make acrylonitrile and propylene from propane.

In Application Ser. No. 049,252, filed May 15, 1987, are disclosed and claimed catalysts containing Sb and V in atomic ratios of Sb:V>1. These catalysts contain tungsten in the preferred catalyst, as well as phosphorus and an inorganic oxide support that improves catalytic activity. These catalysts are used for the reaction of paraffins with ammonia and oxygen to make nitriles plus olefins; especially to make acrylonitrile and propylene from propane.

In Application Ser. No. 047,949, filed May 8, 1987, now U.S. Pat. No. 4,788,317, is disclosed the reaction of paraffins with oxygen and ammonia to olefins and α,β-unsaturated nitriles which also uses a catalyst containing V, Sb, W and a support wherein the atomic Sb:V ratio is greater than 1. These catalysts may advantageously also contain phosphorus.

It is an object of the present invention to provide an improved process for the ammoxidation of paraffins to unsaturated mononitriles and the corresponding mono-olefins.

It is a further object of the invention to provide new catalysts for such reaction.

Still another object is to provide an improved catalytic ammoxidation process for making unsaturated nitriles and olefins from lower paraffins without the use of halogen promoters.

Other objects, as well as aspects, features and advantages, of the present invention will become apparent from a study of the accompanying disclosure and the claims.

These and other objects are achieved by the present invention according to one aspect of which there is provided a process for making $C_3$ to $C_4$ α,β-unsaturated mononitriles and $C_3$ and $C_4$ mono-olefins by the catalytic reaction of a paraffin containing 3 to 4 carbon atoms with oxygen and ammonia by catalytic contact of the foregoing reactants in a reaction zone with a complex metal oxide catalyst having the elements and the proportions which are represented by the following empirical formula:

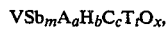

$VSb_mA_aH_bC_cT_tO_x$, where

A is one or more of W, Sn, Mo, B, P and Ge;
H is one or more of Fe, Co, Ni, Cr, Pb, Mn, Zn, Se, Te, Ga, Zr In and As;
C is one or more of an alkali metal and Tl;
T is one or more of Ca, Sr, Mg and Ba; and
where m is 0.01–1; a is 0.2–10; b is 0–10; c is 0–1; t is 0–10; the ratio (a+b+c+t):(1+m) is 0.1–6; no more than 2 atoms of Mo are present per atom of V; wherein x is determined by the oxidation state of the other elements, and wherein the antimony has an average valency higher than +3 and the vanadium has an average valency lower than +5, wherein A includes at least 0.2 atoms of W per atom of V, and wherein the foregoing catalyst contains a support/diluent material selected from silica-alumina and alumina containing 20 to 100 weight percent alumina.

The nitrile products of the present process contain one C to C double bond and one nitrile group. The desired olefin products contain one double bond and the same number of C atoms as the paraffin feed.

In the above catalysts A usually includes at least 0.4 atoms of W per atom of V. Particularly useful are catalysts wherein A includes at least 0.1, usually at least 0.5 atoms of P per atom of V.

Usually, the support/diluent contains 50 to 100 percent alumina, more usually 60 to 100 weight percent alumina.

It should be noted that the present ammoxidation reaction is effected in the substantial absence of halogen or sulfur or compounds thereof. Preferably also, a halide or halogen is not employed in any stage in the preparation of the catalyst. Moreover, the present catalyst does not contain uranium.

The present process is especially useful in the ammoxidation of propane and isobutane.

According to the present invention the foregoing catalysts are prepared under conditions such that in the final composition the average oxidation state of vanadium is less than 5. One method for preparing the catalysts of the present invention involves a redox reaction between a compound of trivalent antimony such as $Sb_2O_3$ and a compound of pentavalent vanadium such as $V_2O_5$, during which at least part of the antimony is oxidized and at least part of the vanadium is reduced.

The redox reaction can conveniently be carried out in an aqueous medium by heating at a temperature of at least 80° C. and up to 200° C., for instance, by heating an aqueous dispersion of a $V^{+5}$ compound, such as $NH_4VO_3$ or $V_2O_5$, with an $Sb^{3+}$ compound, usually in admixture with the inorganic oxide support material, so that the the V has an average valence less than +5 and the reacted Sb has an average valence more than +3.

The resulting catalyst precursor slurry can be dried and calcined in a molecular oxygen containing gas at temperatures of 350° to 850° C., usually 400° to 650° C., to produce a catalyst useful in the process of the invention for ammoxidizing $C_3$ to $C_4$ paraffins. The additives A, H, C and/or T can be added in the slurry after the redox reaction, or the solid particles containing the vanadium and antimony values after separation from the aqueous medium can be coated or impregnated in a known manner with such additives at any suitable stage prior to final calcination of the catalyst.

If the vanadium-antimony catalysts of the invention are prepared by using pentavalent vanadium and pentavalent antimony compounds, thus eliminating the redox reaction, both the vanadium and antimony remain in the high oxidation state and the resulting catalyst is inferior, with or without additives.

Thus, according to the present invention the superior catalytic performance in paraffin ammoxidation to make the corresponding unsaturated mononitrile and olefin, is obtained with the catalysts of the invention which contain a complex vanadium-antimony oxide composition containing tungsten, with vanadium in a low oxidation state less than +5 and antimony in a high oxidation state greater than +3, plus an inorganic oxide support.

Phosphorus and the optional elements shown in formula (1) can be incorporated in the base vanadium/antimony/support precursor slurry or added to the solids recovered from the slurry by methods generally known in the art, using oxides, hydroxides, acids, salts (particularly organic salts such as acetates), and other compounds of such elements. Examples of such incorporation are shown in the specific examples hereinafter.

Tungsten is advantageeously incorporated as ammonium meta- or orthotungstate, tungstic acid, or tungsten trioxide. P can be introduced, for instance, as ammonium phosphate or $(NH_4)_2HPO_4$ or phosphoric acid.

The catalyst support not only improves mechanical stability of the catalysts, but the catalytic activity is significantly improved.

The catalysts of formula (1) can, of course, contain oxides of other elements not set forth in formula (1), as long as they do not materially detrimentally affect the catalytic ammoxidation of the paraffin to the desired nitriles. When bismuth is optionally present in oxidized form as part of the catalyst of formula (1), it is usually present in amounts of no more than 0.2 atoms of Bi per atom of V.

The weight ratio of the catalyst having the ingredients of empirical formula (1) to the support/diluent material can vary from 9:1 to 1:99.

In the process of the present invention, the reaction is preferably carried out in the gas phase by contacting a mixture of the paraffin, ammonia and a molecular oxygen containing gas, such as air, with a catalyst of the invention contained in a fixed bed, a gravity flowing bed, a fluidized bed or a fast transport reactor mode. It also possible to include additional diluents such as steam, nitrogen, carbon dioxide or helium.

The mole ratio of the paraffin, such as propane, to molecular oxygen in the feed to the reaction zone, can vary from 0.1:1 to 10:1, and a ratio in the range from 0.2:1 to 8:1 is more usual. The mole ratio of paraffin, such as propane, to ammonia in the feed to the reaction zone, can vary from 0.2:1 to 16:1, but is usually from 0.4:1 to 8:1. Especially useful results are obtained when operating with a propane to $NH_3$ mole ratio in the range from 2 to 16 and a mole ratio of paraffin to $O_2$ in the range from 1 to 10, so that there is a large excess of paraffin over both $O_2$ and $NH_3$, as compared to stoichiometric requirements to convert the paraffin to the nitrile.

It should be noted that when operating at ratios of paraffin to oxygen and to ammonia in excess of stoichiometric, 100 percent conversion of paraffin is not even theoretically attainable. However, when so operating, an advantage is that the selectivity of the paraffin to the corresponding nitrile and the corresponding olefin is greatly increased, and the olefin product can be further ammoxidized with $O_2$ and $NH_3$ to make further quantities of the nitrile. Thus, the nitrile and the corresponding olefin are both useful products of the present process. The unreacted olefin and paraffin can, of course, be fed to an ammoxidation step.

The reaction temperature can vary from 400° to 650° C., but is usually 460° to 520° C. The latter temperature ranges are especially useful in the case of propane ammoxidation to acrylonitrile.

The average contact time is usually from 0.02 to 20 seconds, and is usually from 0.2 to 8 seconds, but higher or lower contact times can be used.

Harris in U.S. Pat. No. 3,860,534 discloses the ammoxidation of alkanes with catalysts containing only V and Sb, in oxide form, which are water-washed after calcination. The present catalysts are not water washed, and the combination of tungsten and a support containing alumina distinguishes this patent.

British Pat. No. 1,336,136 discloses ammoxidation of alkane with a catalyst containing V and Sb in oxide form and also optionally containing one further metallic oxide (only Sn is named). It is said that a support can be used, while naming no support. British Pat. No. 1,336,135 is a similar companion patent that discloses two and three-component oxide catalysts, including some having both V and Sb. Neither discloses that tungsten or alumina (support) can be in such catalysts.

None of the foregoing patents discloses the presence of V having an average valence lower than +5.

Canadian Pat. No. 901,006, also directed to alkane ammoxidation, discloses catalysts containing any 3 metals in the oxide form selected from Sb, Sn, Ti, V and U, except the combination Sb-Sn-V. Again, this patent discloses no V/Sb catalyst containing W, or a catalyst containing a support containing alumina, nor a catalyst having V with an average valence less than +5.

Shaw U.S. Pat. No. 4,138,366 discloses conversion of unsaturated aldehydes to unsaturated acids using a catalyst containing and Mo, Sb and V containing a support material that may be alumina, but W is not among the optional elements recited.

For the same reaction U.S. Pat. Nos. 3,773,692 and 3,867,345 disclose catalysts containing Mo, V, Sb and W.

These patents both say that aluminum oxide and silicon dioxide are suitable supports. However, both patents prefer $SiO_2$, diatomite and/or montmorillonnite, and no example uses a high alumina support. All examples of both patents have ratios of Mo:V far outside the present claims. Neither patent, moreover, suggests catalysts having V with an average valence less than +5 or Sb with an average valence more than +3.

Decker U.S. Pat. No. 3,637,797 discloses making aromatic nitriles by reacting alkyl-substituted aromatic hydrocarbons with ammonia and molecular oxygen in the presence of catalysts containing oxides of V, Sb, alkali metal, Fe (optional) and tungsten (optional) and aluminum oxide, wherein the V is +5 valence and the Sb is +3 valence.

The following examples of the invention are exemplary and should not be taken as in any way limiting.

In the examples the conversion, yield and selectivity are defined as follows:

$$\text{conversion} = \frac{\text{moles paraffin reacted}}{\text{moles paraffin charged}} \times 100\ (\%)$$

$$\text{yield} = \frac{\text{moles product produced}}{\text{moles paraffin charged}} \times 100\ (\%)$$

$$\text{selectivity} = \frac{\text{moles product produced}}{\text{moles paraffin reacted}} \times 100\ (\%)$$

EXAMPLE 1

A catalyst having the empirical composition 50 wt % VSbPWO$_x$—50 wt % Al$_2$O$_3$ was made as follows:

Ammonium meta-vanadate (5.48 g) and ammonium meta-tungstate (12.64 g) were dissolved in ~100 cc of hot water. 85% phosphoric acid (5.34 g) was then added to the above solution along with an additional 20–30 cc of water, turning the solution from yellow to a deep burgundy red. While rapidly stirring the red solution from above, antimony trioxide (6.75 g) was added, resulting in an initial red/orange slurry. This slurry was covered and allowed to "reflux" for one hour after which the color changed to a dark blue/green.

In a separate beaker, Catapal SB Al$_2$O$_3$ (29.41 g=25.0 g Al$_2$O$_3$) was slurried in 100 cc H$_2$O and peptized with glacial acetic acid (4.2 g) to form a sol-like dispersed alumina. After aging for 1 hour, this dispersion was slowly added to the blue/green slurry from above along with enough water to prevent the slurry from gelling up (~100 cc). The resulting blue/green slurry was then evaporated to near dryness on a hot plate, and the thick bluish paste obtained was further dried at 110° C. for ~16 hrs. A heat treatment of 350° C. for 5 hours was carried out on the dried catalyst precursor, followed by crushing and screening to 20–35 mesh particles. A portion of the sieved material was then subjected to a final calcination of 610° C. for 3 hours.

EXAMPLE 2

A catalyst having the empirical composition 50 wt % VSb$_{0.5}$PWO$_x$-50 wt % Al$_2$O$_3$ was made exactly as in Example 29 but using the following amounts of the batch materials:

| | |
|---|---|
| NH$_4$VO$_3$ | 7.16 g |
| Ammonium Meta-tungstate | 16.70 g |
| 85% H$_3$PO$_4$ | 7.06 g |
| Sb$_2$O$_3$ | 0.89 g |
| Al$_2$O$_3$ (catapal SB alumina) | 29.41 g |

EXAMPLE 3

A catalyst having the empirical composition 50 wt % VSb$_{0.5}$P$_{1.5}$WO$_x$-50 wt % Al$_2$O$_3$ was made as follows:

Ammonium meta-vanadate (5.82 g) and ammonium meta-tungstate (14.62 g) were dissolved in ~100 cc of hot water. 85% phosphoric acid (6.18 g) was then added to the above solution along with an additional 20–30 cc of water, turning the solution from yellow to a deep burgundy red. While rapidly stirring the red solution from above, antimony trioxide was added resulting in an initial red/orange slurry. This slurry was covered and allowed to "reflux" for one hour after which the color has changed to a dark blue/green.

In a separate beaker, Catapal SB Al$_2$O$_3$ (29.41 g=25.0 g Al$_2$O$_3$) was slurried in 100 cc H$_2$O and peptized with glacial acetic acid (4.5 g) to form a sol-like dispersed alumina. After aging for 1 hour, this dispersion was slowly added to the blue/green slurry from above along with enough water to prevent the slurry from gelling up (~100 cc). The resulting blue/green slurry was evaporated to near dryness on a hot plate, and the thick bluish paste obtained further dried at 110° C. for ~16 hrs. A heat treatment of 350° C. for 5 hours was carried out on the dried catalyst precursor, followed by crushing and screening to 20–35 mesh particles. A portion of the sieved material was then subjected to a final calcination of 610° C. for 3 hours.

EXAMPLE 4

A catalyst having the empirical composition 50 wt% VSb$_{0.1}$PWO$_x$-50 wt% Al$_2$O$_3$ was made as follows:

Ammonium meta-vanadate (7.16 g) and ammonium meta-tungstate (16.70 g) were dissolved in ~100 cc of hot water. 85% phosphoric acid (7.06 g) was then added to the above solution along with an additional 20–30 cc of water, turning the solution from yellow to a deep burgundy red. While rapidly stirring the red solution from above, antimony trioxide (0.89 g) was added resulting in an initial red/orange slurry. This slurry was covered and allowed to "reflux" for one hour after which the color has changed to a dark blue/green.

In a separate beaker, Catapal SB Al$_2$O$_3$ (29.41 g=25.0 g Al$_2$O$_3$) was slurried in 100 cc H$_2$O and peptized with glacial acetic acid (4.5 g) to form a sol-like dispersed alumina. After aging for 1 hour, this dispersion was slowly added to the blue/green slurry from above along with enough water to prevent the slurry from gelling up (~100 cc). The resulting blue/green slurry was evaporated to near dryness on a hot plate, and the thick bluish paste obtained further dried at 110° C. for ~16 hours. A heat treatment of 350° C. for 5 hours was carried out on the dried catalyst precursor, followed by crushing and screening to 20–35 mesh particles. A portion of the sieved material was then subjected to a final calcination of 610° C. for 3 hours.

EXAMPLE 5

A catalyst having the empirical composition 50 wt% VSb$_{0.1}$P$_{1.5}$WO$_x$-50 wt% Al$_2$O$_3$ was made as follows:

Ammonium meta-vanadate (6.59 g) and ammonium meta-tungstate (15.37 g) were dissolved in ~100 cc of hot water. 85% phosphoric acid (9.74 g) was then added to the above solution along with an additional 20–30 cc of water, turning the solution from yellow to a deep burgundy red. While rapidly stirring the red solution from above, antimony trioxide (0.82 g) was added resulting in an initial red/orange slurry. This slurry was covered and allowed to "reflux" for one hour after which the color has changed to a dark blue/green.

In a separate beaker, Catapal SB Al$_2$O$_3$ (29.41 g=25.0 g Al$_2$O$_3$) was slurried in 100 cc H$_2$O and peptized with glacial acetic acid (4.5 g) to form a sol-like dispersed alumina. After aging for 1 hour, this dispersion was slowly added to the blue/green slurry from above along with enough water to prevent the slurry from gelling up (~100 cc). The resulting blue/green slurry was evaporated to near dryness on a hot plate, and the thick bluish paste obtained further dried at 110° C. for ~16 hrs. A heat treatment of 350° C. for 5 hours was carried out on the dried catalyst precursor, followed by crushing and screening to 20–35 mesh particles. A portion of the sieved material was then subjected to a final calcination of 610° C. for 3 hours.

In the ammoxidation runs of the following examples, the catalyst is in a tubular ⅜ inch I.D. stainless steel fixed bed reactor. The reactor is equipped with a preheat leg immersed in a temperature controlled molten salt bath. The feed is fed to the catalyst for one hour before the runs are started and product is collected and analyzed; the runs of each example last 30–60 minutes.

EXAMPLE 6

The gaseous feed components were metered through mass flow controllers into the bottom of the reactor through the preheat leg. The catalyst was the catalyst of Example 1. Water was introduced through a septum at the top of the preheat leg, using a syrine pump. The reaction temperature was 470° C. and the molar feed ratios were 5 propane/1NH$_3$/2O$_2$/1H$_2$O. The contact time was 0.2 seconds. Analysis of the reactor effluent showed the propane conversion was 20.7 percent; yield and selectivity of propane to acrylonitrile were 4.0% and 19.5%, respectively; selectivity to propylene was 52.1%.

EXAMPLE 7

The gaseous feed components were metered through mass flow controllers into the bottom of the reactor through the preheat leg. The catalyst was the catalyst of Example 2. Water was introduced through a septum at the top of the preheat leg, using a syringe pump. The reaction temperature was 470° C. and the molar feed ratios were 5 propane/1NH$_3$/2O$_2$/1H$_2$O. The contact time was 0.3 seconds. Analysis of the reactor effluent showed that the propane conversion was 20.4 percent; yield and selectivity of propane to acrylonitrile were 4.1 and 20.1 percent, respectively; selectivity to propylene was 48.6 percent.

EXAMPLE 8

The gaseous feed components were metered through mass flow controllers into the bottom of the reactor through the preheat leg. The catalyst was the catalyst of Example 3. Water was introduced through a septum at the top of the preheat leg, using a syringe pump. The reaction temperature was 470° C. and the molar feed ratios were 5 propane/1NH$_3$/2O$_2$/1H$_2$O. The contact time was 0.2 seconds. Analysis of the reactor effluent showed that propane conversion was 21.0 percent; yield and selectivity of propane to acrylonitrile were 4.3 and 20.6 percent, respectively; selectivity to propylene was 49.5 percent.

EXAMPLE 9

The gaseous feed components were metered through mass flow controllers into the bottom of the reactor through the preheat leg. The catalyst was the catalyst of Example 5. Water was introduced through a septum at the top of the preheat leg, using a syringe pump. The reaction temperature was 470° C. and the molar feed ratios were 5 propane/1NH$_3$/2O$_2$/1H$_2$O. The contact time was 0.3 seconds. Analysis of the reactor effluent showed that propane conversion was 21.0 percent; yield and selectivity of propane to acrylonitrile were 3.7 and 17.8 percent, respectively; selectivity to propylene was 47.4 percent.

EXAMPLE 10

The gaseous feed components were metered through mass flow controllers into the bottom of the reactor through the preheat leg. The catalyst was the catalyst of Example 4. Water was introduced through a septum at the top of the preheat leg, using a syringe pump. The reaction temperature was 470° C. and the molar feed ratios were 5 propane/1NH$_3$/2O$_2$/1H$_2$O. The contact time was 0.3 seconds. Analysis of the reactor effluent showed that propane conversion was 20.5 percent; yield and selectivity of propane to acrylonitrile were 3.5 and 17.0 percent, respectively; selectivity to propylene was 48.6 percent.

The following are additional catalyst compositions of the invention containing promoting amounts of phosphorus. When these are used under the conditions of Example 7 to ammoxidize propane, similarly high total selectivities to acrylonitrile plus propylene result.

50 wt% VSbSn$_{0.5}$Te$_{0.5}$Fe$_{0.5}$P$_{0.5}$WO$_x$+50 wt% Al$_2$O$_3$ 50 wt% VSb$_{0.8}$P$_{0.5}$W$_{0.5}$Mo$_{0.5}$O$_x$+50 wt% Al$_2$O$_3$ 50 wt% VSb$_{0.6}$P$_{0.5}$W$_3$O$_x$+25 wt% Al$_2$O$_3$+25 wt% SiO$_2$ 50 wt% VSbCoNiP$_{0.5}$WO$_x$+50 wt% Al$_2$O$_3$ 50 wt% VSb$_{0.6}$PWO$_x$+40 wt% Al$_2$O$_3$+10 wt% SiO$_2$ 50 wt% VSb$_{0.5}$P$_{0.5}$WCs$_{0.01}$O$_x$+50 wt% Al$_2$O$_3$ 50 wt% VSbP$_3$CrWO$_x$+40 wt% Al$_2$O$_3$+10 wt% SiO$_2$ 50 wt% VSbP$_{0.5}$W$_3$O$_x$+40 wt% Al$_2$O$_3$+10 wt% SiO$_2$.

As will be evident to those skilled in the art, various modifications of this invention can be made or followed in the light of the foregoing disclosure and discussion without departing from the spirit and scope of the disclosure or from the scope of the claims.

We claim:

1. A complex metal oxide catalyst having the elements and proportions which are represented by the following empirical formula:

$$VSb_mA_aH_bC_cT_tO_x,$$

where
A is one or more of W, Sn, Mo, B, P and Ge;
H is one or more of Fe, Co, Ni, Cr, Pb, Mn, Zn, Se, Te, Ga, Zr, In and As;
C is one or more of an alkali metal and Tl;
T is one or more of Ca, Sr, Mg and Ba; and
where m is 0.1–1; a is 0.7–10; b is 0–10; c is 0–1; t is 0–10; the ratio (a+b+c+t):(1+m) is 0.1–6; no more than 2 atoms of Mo are present per atom of V; wherein x is determined by the oxidation state of the other elements, and wherein the antimony has an average valency higher than +3 and the vanadium has an average valency lower than +5, wherein A includes at least 0.2 atom of W per atom of V and at least 0.5 atom of P per atom of V, and wherein the foregoing catalyst contains a support/diluent material selected from silica-alumina and alumina containing 20 to 100 weight percent alumina.

2. A catalyst of claim 1 which contains at least 0.4 atom of W per atom of V.

3. A catalyst of claim 2 wherein said support/diluent contains 50–100 weight percent alumina.

4. A catalyst of claim 2 wherein said support/diluent contains 60–100 weight percent alumina.

UNITED STATES PATENT AND TRADEMARK OFFICE
CERTIFICATE OF CORRECTION

PATENT NO.  : 4,871,706

DATED       : October 3, 1989

INVENTOR(S) : James F. Brazdil, Jr., et al.

It is certified that error appears in the above-identified patent and that said Letters Patent is hereby corrected as shown below:

Column 5, line 34, change "29" to -- 1 --.

Column 8, line 48, (claim 1, line 11) change "m is 0.1-1" to -- m is 0.01 to 1 --.

Signed and Sealed this

Second Day of March, 1993

Attest:

STEPHEN G. KUNIN

Attesting Officer

Acting Commissioner of Patents and Trademarks